(12) United States Patent
Knick et al.

(10) Patent No.: US 11,014,967 B2
(45) Date of Patent: May 25, 2021

(54) ALKALINE STABLE FC-BINDING PROTEINS FOR AFFINITY CHROMATOGRAPHY

(71) Applicant: Repligen Corporation, Waltham, MA (US)

(72) Inventors: Paul Knick, Halle/Saale (DE); Erik Fiedler, Halle/Saale (DE); Ulrich Haupts, Halle/Saale (DE); Maren Meysing, Halle/Saale (DE)

(73) Assignee: Repligen Corporation, Waltham, MA (US)

( * ) Notice: Subject to any disclaimer, the term of this patent is extended or adjusted under 35 U.S.C. 154(b) by 0 days.

(21) Appl. No.: 16/324,842

(22) PCT Filed: Aug. 7, 2017

(86) PCT No.: PCT/EP2017/069979
§ 371 (c)(1),
(2) Date: Feb. 11, 2019

(87) PCT Pub. No.: WO2018/029158
PCT Pub. Date: Feb. 15, 2018

(65) Prior Publication Data
US 2019/0300568 A1    Oct. 3, 2019

(30) Foreign Application Priority Data

Aug. 11, 2016  (EP) ..................................... 16183710
Dec. 21, 2016  (EP) ..................................... 16205707

(51) Int. Cl.
| | | |
|---|---|---|
| *C07K 1/22* | (2006.01) | |
| *C07K 14/31* | (2006.01) | |
| *C07K 17/00* | (2006.01) | |
| *C07K 16/06* | (2006.01) | |

(52) U.S. Cl.
CPC ................ *C07K 14/31* (2013.01); *C07K 1/22* (2013.01); *C07K 16/065* (2013.01); *C07K 17/00* (2013.01)

(58) Field of Classification Search
CPC .................................. C07K 16/06; C07K 1/22
See application file for complete search history.

(56) References Cited

FOREIGN PATENT DOCUMENTS

| | | |
|---|---|---|
| EP | 2690173 A1 | 1/2014 |
| WO | 2015/005859 A1 | 1/2015 |
| WO | 2016-079033 A1 | 5/2016 |

OTHER PUBLICATIONS

International Search Report and Written Opinion dated Nov. 24, 2017 for PCT/EP2017/069979 filed Aug. 7, 2017.

*Primary Examiner* — Karen Cochrane Carlson
(74) *Attorney, Agent, or Firm* — Kacvinsky Daisak Bluni PLLC

(57) ABSTRACT

The present invention relates to Fc binding proteins comprising one or more Fc binding domains wherein at least one domain comprises of an amino acid sequence selected from the group consisting of SEQ ID NOs: 1-6 or 21. The invention further relates to affinity matrices comprising the Fc binding proteins of the invention. The invention also relates to a use of these Fc binding proteins or affinity matrices for affinity purification of immunoglobulins and to methods of affinity purification using the Fc binding proteins of the invention.

14 Claims, 4 Drawing Sheets
Specification includes a Sequence Listing.

A.

B.

A.

B.

| Ligand | Resin | Elution at 0.1M Citrat pH 3.5 [%] | Elution at 0.1M Citrat pH 2.0 [%] |
|---|---|---|---|
| cs24 | Purolite 45 | 98,5 | 1,5 |
| cs24a | Purolite 45 | 99,5 | 0,5 |
| cs24b | Purolite 45 | 99,7 | 0,2 |
| C-Domain | Purolite 45 | 89,7 | 10,3 |
| cs26 | Purolite 45 | 98,4 | 1,6 |
| cs26a | Purolite 45 | 99,2 | 0,8 |
| cs26b | Purolite 45 | 99,6 | 0,4 |
| cs26 | Purolite 85 | 99,1 | 0,9 |
| cs26a | Purolite 85 | 99,6 | 0,4 |
| cs24 | Purolite 85 | 99 | 1 |
| C-Domain | Purolite 85 | 90,4 | 9,6 |

SEQUENCE LISTING

<160> NUMBER OF SEQ ID NOS: 22

<210> SEQ ID NO 1
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs24

<400> SEQUENCE: 1

Ile Ala Ala Gln His Asp Lys Glu Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs26

<400> SEQUENCE: 2

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 3
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs24a

<400> SEQUENCE: 3

Ile Ala Ala Gln His Asp Lys Glu His Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Lys
    50                  55

<210> SEQ ID NO 4

```
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs26a

<400> SEQUENCE: 4

Ile Ala Ala Gln His Asp Lys Asp His Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 5
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs24b

<400> SEQUENCE: 5

Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg His Asp Pro Ser Val Ser Leu Glu Ile Leu Gly Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs26b

<400> SEQUENCE: 6

Ile Ala Ala Gln His Asp Lys Asp Gln Gln Ala Ala Phe Tyr Glu Ile
1               5                   10                  15

Leu His Leu Pro Asn Leu Thr Glu Gln Gln Arg Asn Ala Phe Ile Gln
            20                  25                  30

Ser Leu Arg His Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 7
<211> LENGTH: 53
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<223> OTHER INFORMATION: cs24 delNC

<400> SEQUENCE: 7

Gln His Asp Lys Glu Gln Gln Ala Ala Phe Tyr Glu Ile Leu His Leu
1               5                   10                  15

Pro Asn Leu Thr Glu Asp Gln Arg Asn Ala Phe Ile Gln Ser Leu Arg
            20                  25                  30

Asp Asp Pro Ser Val Ser Leu Glu Ile Leu Gly Glu Ala Lys Lys Leu
        35                  40                  45

Asn Asp Ala Gln Ala
    50

<210> SEQ ID NO 8
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs26 delNC

<400> SEQUENCE: 8

Gln His Asp Lys Asp Gln Gln Ala Ala Phe Tyr Glu Ile Leu His Leu
1               5                   10                  15

Pro Asn Leu Thr Glu Glu Gln Arg Asn Ala Phe Ile Gln Ser Leu Arg
            20                  25                  30

Asp Asp Pro Ser Val Ser Leu Glu Ile Leu Ala Glu Ala Lys Lys Leu
        35                  40                  45

Asn Asp Ala Gln Ala
    50

<210> SEQ ID NO 9
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs24 delN

<400> SEQUENCE: 9

Ala His Asp Lys Glu Gln Gln Ala Ala Phe Tyr Glu Ile Leu His Leu
1               5                   10                  15

Pro Asn Leu Thr Glu Asp Gln Arg Asn Ala Phe Ile Gln Ser Leu Arg
            20                  25                  30

Asp Asp Pro Ser Val Ser Leu Glu Ile Leu Gly Glu Ala Lys Lys Leu
        35                  40                  45

Asn Asp Ala Gln Ala Pro Lys
    50                  55

<210> SEQ ID NO 10
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs26 delN
```

<400> SEQUENCE: 10

Ala His Asp Lys Asp Gln Gln Ala Ala Phe Tyr Glu Ile Leu His Leu
1               5                   10                  15

Pro Asn Leu Thr Glu Glu Gln Arg Asn Ala Phe Ile Gln Ser Leu Arg
            20                  25                  30

Asp Asp Pro Ser Val Ser Leu Glu Ile Leu Ala Glu Ala Lys Lys Leu
        35                  40                  45

Asn Asp Ala Gln Ala Pro Lys
    50                  55

<210> SEQ ID NO 11
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs24 delNC hexamer

<400> SEQUENCE: 11

Gln His Asp Lys Glu Gln Gln Ala Ala Phe Tyr Glu Ile Leu His Leu
1               5                   10                  15

Pro Asn Leu Thr Glu Asp Gln Arg Asn Ala Phe Ile Gln Ser Leu Arg
            20                  25                  30

Asp Asp Pro Ser Val Ser Leu Glu Ile Leu Gly Glu Ala Lys Lys Leu
        35                  40                  45

Asn Asp Ala Gln Ala Gln His Asp Lys Glu Gln Gln Ala Ala Phe Tyr
    50                  55                  60

Glu Ile Leu His Leu Pro Asn Leu Thr Glu Asp Gln Arg Asn Ala Phe
65                  70                  75                  80

Ile Gln Ser Leu Arg Asp Asp Pro Ser Val Ser Leu Glu Ile Leu Gly
                85                  90                  95

Glu Ala Lys Lys Leu Asn Asp Ala Gln Ala Gln His Asp Lys Glu Gln
            100                 105                 110

Gln Ala Ala Phe Tyr Glu Ile Leu His Leu Pro Asn Leu Thr Glu Asp
        115                 120                 125

Gln Arg Asn Ala Phe Ile Gln Ser Leu Arg Asp Asp Pro Ser Val Ser
    130                 135                 140

Leu Glu Ile Leu Gly Glu Ala Lys Lys Leu Asn Asp Ala Gln Ala Gln
145                 150                 155                 160

His Asp Lys Glu Gln Gln Ala Ala Phe Tyr Glu Ile Leu His Leu Pro
                165                 170                 175

Asn Leu Thr Glu Asp Gln Arg Asn Ala Phe Ile Gln Ser Leu Arg Asp
            180                 185                 190

Asp Pro Ser Val Ser Leu Glu Ile Leu Gly Glu Ala Lys Lys Leu Asn
        195                 200                 205

Asp Ala Gln Ala Gln His Asp Lys Glu Gln Gln Ala Ala Phe Tyr Glu
    210                 215                 220

Ile Leu His Leu Pro Asn Leu Thr Glu Asp Gln Arg Asn Ala Phe Ile
225                 230                 235                 240

Gln Ser Leu Arg Asp Asp Pro Ser Val Ser Leu Glu Ile Leu Gly Glu
                245                 250                 255

Ala Lys Lys Leu Asn Asp Ala Gln Ala Gln His Asp Lys Glu Gln Gln
            260                 265                 270

```
Ala Ala Phe Tyr Glu Ile Leu His Leu Pro Asn Leu Thr Glu Asp Gln
            275                 280                 285

Arg Asn Ala Phe Ile Gln Ser Leu Arg Asp Asp Pro Ser Val Ser Leu
            290                 295                 300

Glu Ile Leu Gly Glu Ala Lys Lys Leu Asn Asp Ala Gln Ala
305                 310                 315

<210> SEQ ID NO 12
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs26 delNC hexamer

<400> SEQUENCE: 12

Gln His Asp Lys Asp Gln Gln Ala Ala Phe Tyr Glu Ile Leu His Leu
1               5                   10                  15

Pro Asn Leu Thr Glu Glu Gln Arg Asn Ala Phe Ile Gln Ser Leu Arg
            20                  25                  30

Asp Asp Pro Ser Val Ser Leu Glu Ile Leu Ala Glu Ala Lys Lys Leu
            35                  40                  45

Asn Asp Ala Gln Ala Gln His Asp Lys Asp Gln Gln Ala Ala Phe Tyr
        50                  55                  60

Glu Ile Leu His Leu Pro Asn Leu Thr Glu Glu Gln Arg Asn Ala Phe
65                  70                  75                  80

Ile Gln Ser Leu Arg Asp Asp Pro Ser Val Ser Leu Glu Ile Leu Ala
                85                  90                  95

Glu Ala Lys Lys Leu Asn Asp Ala Gln Ala Gln His Asp Lys Asp Gln
            100                 105                 110

Gln Ala Ala Phe Tyr Glu Ile Leu His Leu Pro Asn Leu Thr Glu Glu
            115                 120                 125

Gln Arg Asn Ala Phe Ile Gln Ser Leu Arg Asp Asp Pro Ser Val Ser
        130                 135                 140

Leu Glu Ile Leu Ala Glu Ala Lys Lys Leu Asn Asp Ala Gln Ala Gln
145                 150                 155                 160

His Asp Lys Asp Gln Gln Ala Ala Phe Tyr Glu Ile Leu His Leu Pro
                165                 170                 175

Asn Leu Thr Glu Glu Gln Arg Asn Ala Phe Ile Gln Ser Leu Arg Asp
            180                 185                 190

Asp Pro Ser Val Ser Leu Glu Ile Leu Ala Glu Ala Lys Lys Leu Asn
            195                 200                 205

Asp Ala Gln Ala Gln His Asp Lys Asp Gln Gln Ala Ala Phe Tyr Glu
        210                 215                 220

Ile Leu His Leu Pro Asn Leu Thr Glu Glu Gln Arg Asn Ala Phe Ile
225                 230                 235                 240

Gln Ser Leu Arg Asp Asp Pro Ser Val Ser Leu Glu Ile Leu Ala Glu
                245                 250                 255

Ala Lys Lys Leu Asn Asp Ala Gln Ala Gln His Asp Lys Asp Gln Gln
            260                 265                 270

Ala Ala Phe Tyr Glu Ile Leu His Leu Pro Asn Leu Thr Glu Glu Gln
            275                 280                 285

Arg Asn Ala Phe Ile Gln Ser Leu Arg Asp Asp Pro Ser Val Ser Leu
            290                 295                 300
```

```
Glu Ile Leu Ala Glu Ala Lys Lys Leu Asn Asp Ala Gln Ala
305                 310                 315
```

<210> SEQ ID NO 13
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs24 pentamer

<400> SEQUENCE: 13

```
Ile Ala Ala Gln His Asp Lys Glu Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Lys Ile Ala Ala Gln His Asp
50                  55                  60

Lys Glu Gln Gln Ala Ala Phe Tyr Glu Ile Leu His Leu Pro Asn Leu
65                  70                  75                  80

Thr Glu Asp Gln Arg Asn Ala Phe Ile Gln Ser Leu Arg Asp Asp Pro
                85                  90                  95

Ser Val Ser Leu Glu Ile Leu Gly Glu Ala Lys Lys Leu Asn Asp Ala
            100                 105                 110

Gln Ala Pro Lys Ile Ala Ala Gln His Asp Lys Glu Gln Gln Ala Ala
        115                 120                 125

Phe Tyr Glu Ile Leu His Leu Pro Asn Leu Thr Glu Asp Gln Arg Asn
130                 135                 140

Ala Phe Ile Gln Ser Leu Arg Asp Asp Pro Ser Val Ser Leu Glu Ile
145                 150                 155                 160

Leu Gly Glu Ala Lys Lys Leu Asn Asp Ala Gln Ala Pro Lys Ile Ala
                165                 170                 175

Ala Gln His Asp Lys Glu Gln Gln Ala Ala Phe Tyr Glu Ile Leu His
            180                 185                 190

Leu Pro Asn Leu Thr Glu Asp Gln Arg Asn Ala Phe Ile Gln Ser Leu
        195                 200                 205

Arg Asp Asp Pro Ser Val Ser Leu Glu Ile Leu Gly Glu Ala Lys Lys
210                 215                 220

Leu Asn Asp Ala Gln Ala Pro Lys Ile Ala Ala Gln His Asp Lys Glu
225                 230                 235                 240

Gln Gln Ala Ala Phe Tyr Glu Ile Leu His Leu Pro Asn Leu Thr Glu
                245                 250                 255

Asp Gln Arg Asn Ala Phe Ile Gln Ser Leu Arg Asp Asp Pro Ser Val
            260                 265                 270

Ser Leu Glu Ile Leu Gly Glu Ala Lys Lys Leu Asn Asp Ala Gln Ala
        275                 280                 285

Pro Lys
    290
```

<210> SEQ ID NO 14
<211> LENGTH: 290
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<223> OTHER INFORMATION: cs26 pentamer

<400> SEQUENCE: 14

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys Ile Ala Ala Gln His Asp
50                  55                  60

Lys Asp Gln Gln Ala Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Leu Glu Ile Leu Ala Glu Ala Lys Lys Leu Asn Asp Ala
            100                 105                 110

Gln Ala Pro Lys Ile Ala Ala Gln His Asp Lys Asp Gln Gln Ala Ala
        115                 120                 125

Phe Tyr Glu Ile Leu His Leu Pro Asn Leu Thr Glu Glu Gln Arg Asn
130                 135                 140

Ala Phe Ile Gln Ser Leu Arg Asp Asp Pro Ser Val Ser Leu Glu Ile
145                 150                 155                 160

Leu Ala Glu Ala Lys Lys Leu Asn Asp Ala Gln Ala Pro Lys Ile Ala
                165                 170                 175

Ala Gln His Asp Lys Asp Gln Gln Ala Ala Phe Tyr Glu Ile Leu His
            180                 185                 190

Leu Pro Asn Leu Thr Glu Glu Gln Arg Asn Ala Phe Ile Gln Ser Leu
        195                 200                 205

Arg Asp Asp Pro Ser Val Ser Leu Glu Ile Leu Ala Glu Ala Lys Lys
210                 215                 220

Leu Asn Asp Ala Gln Ala Pro Lys Ile Ala Ala Gln His Asp Lys Asp
225                 230                 235                 240

Gln Gln Ala Ala Phe Tyr Glu Ile Leu His Leu Pro Asn Leu Thr Glu
                245                 250                 255

Glu Gln Arg Asn Ala Phe Ile Gln Ser Leu Arg Asp Asp Pro Ser Val
            260                 265                 270

Ser Leu Glu Ile Leu Ala Glu Ala Lys Lys Leu Asn Asp Ala Gln Ala
        275                 280                 285

Pro Lys
    290

<210> SEQ ID NO 15
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs24 tetramer

<400> SEQUENCE: 15

Ile Ala Ala Gln His Asp Lys Glu Gln Gln Ala Ala Phe Tyr Glu Ile
1               5                   10                  15
```

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Lys Ile Ala Ala Gln His Asp
50                  55                  60

Lys Glu Gln Gln Ala Ala Phe Tyr Glu Ile Leu His Leu Pro Asn Leu
65                  70                  75                  80

Thr Glu Asp Gln Arg Asn Ala Phe Ile Gln Ser Leu Arg Asp Asp Pro
                85                  90                  95

Ser Val Ser Leu Glu Ile Leu Gly Glu Ala Lys Lys Leu Asn Asp Ala
            100                 105                 110

Gln Ala Pro Lys Ile Ala Ala Gln His Asp Lys Glu Gln Gln Ala Ala
            115                 120                 125

Phe Tyr Glu Ile Leu His Leu Pro Asn Leu Thr Glu Asp Gln Arg Asn
    130                 135                 140

Ala Phe Ile Gln Ser Leu Arg Asp Asp Pro Ser Val Ser Leu Glu Ile
145                 150                 155                 160

Leu Gly Glu Ala Lys Lys Leu Asn Asp Ala Gln Ala Pro Lys
                165                 170

<210> SEQ ID NO 16
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs26 tetramer

<400> SEQUENCE: 16

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys Ile Ala Ala Gln His Asp
50                  55                  60

Lys Asp Gln Gln Ala Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Leu Glu Ile Leu Ala Glu Ala Lys Lys Leu Asn Asp Ala
            100                 105                 110

Gln Ala Pro Lys Ile Ala Ala Gln His Asp Lys Asp Gln Gln Ala Ala
            115                 120                 125

Phe Tyr Glu Ile Leu His Leu Pro Asn Leu Thr Glu Glu Gln Arg Asn
    130                 135                 140

Ala Phe Ile Gln Ser Leu Arg Asp Asp Pro Ser Val Ser Leu Glu Ile
145                 150                 155                 160

Leu Ala Glu Ala Lys Lys Leu Asn Asp Ala Gln Ala Pro Lys
                165                 170

<210> SEQ ID NO 17

```
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IB24 parental

<400> SEQUENCE: 17

Ala Ala Ala Gln His Asp Lys Glu Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Lys
    50                  55

<210> SEQ ID NO 18
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IB26 parental

<400> SEQUENCE: 18

Ala Ala Ala Gln His Asp Lys Asp Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: coupling sequence

<400> SEQUENCE: 19

Ala Ser Pro Ala Pro Ser Ala Pro Ser Ala Cys
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: streptaq

<400> SEQUENCE: 20

Trp Ser His Pro Gln Phe Glu Lys
1               5
```

```
<210> SEQ ID NO 21
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cs26c

<400> SEQUENCE: 21

Ile Ala Ala Gln His Asp Lys Asp Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Ser Cys
1               5
```

ALKALINE STABLE FC-BINDING PROTEINS FOR AFFINITY CHROMATOGRAPHY

SEQUENCE LISTING

The instant application contains a Sequence Listing which has been filed electronically in ASCII format and is hereby incorporated by reference in its entirety. Said ASCII copy, created on Feb. 28, 2019, is named 1580_00028_SL.txt and is 24,097 bytes in size.

FIELD OF THE INVENTION

The present invention relates to Fc binding proteins comprising one or more Fc binding domains wherein at least one domain comprises of an amino acid sequence selected from the group consisting of SEQ ID NOs: 1-6 or 21. The invention further relates to affinity matrices comprising the Fc binding proteins of the invention. The invention also relates to a use of these Fc binding proteins or affinity matrices for affinity purification of immunoglobulins and to methods of affinity purification using the Fc binding proteins of the invention.

BACKGROUND OF THE INVENTION

Many biotechnological and pharmaceutical applications require the removal of contaminants from a sample containing antibodies. An established procedure for capturing and purifying antibodies is affinity chromatography using the bacterial cell surface Protein A from *Staphylococcus aureus* as selective ligand for immunoglobulins (see, for example, review by Huse et al., J. Biochem. Biophys. Methods 51, 2002: 217-231). Wild-type Protein A binds to the Fc region of IgG molecules with high affinity and selectivity and is stable at high temperatures and in a wide range of pH values. Variants of Protein A with improved properties such as alkaline stability are available for purifying antibodies and various chromatographic matrices comprising Protein A ligands are commercially available. However, in particular wild-type Protein A based chromatography matrices show a loss of binding capacity for immunoglobulins following exposure to alkaline conditions.

TECHNICAL PROBLEMS UNDERLYING THE PRESENT INVENTION

Most large scale production processes for antibodies or Fc-containing fusion proteins use Protein A for affinity purification. However, due to limitations of Protein A applications in affinity chromatography there is a need in the art to provide novel Fc binding proteins with improved properties that specifically bind to immunoglobulins in order to facilitate affinity purification of immunoglobulins. To maximally exploit the value of the chromatographic matrices comprising Fc binding proteins it is desirable to use the affinity ligand matrices multiple times. Between chromatography cycles, a thorough cleaning procedure is required for sanitization and removal of residual contaminants on the matrix. In this procedure, it is general practice to apply alkaline solutions with high concentrations of NaOH to the affinity ligand matrices. Wild-type Protein A domains cannot withstand such harsh alkaline conditions for an extended time and quickly lose binding capacity for immunoglobulin.

Accordingly, there is an ongoing need in this field to obtain novel alkaline-stable proteins capable of binding immunoglobulins.

The present invention provides alkaline stable immunoglobulin binding proteins that are particularly well-suited for affinity purification of immunoglobulins but overcome the disadvantages of the prior art. In particular, a significant advantage of the alkaline stable Fc binding proteins of the invention is their improved stability at high pH, for example compared to wild type protein A or to a parental protein.

The above overview does not necessarily describe all problems solved by the present invention.

SUMMARY OF THE INVENTION

A first aspect of the present invention is to provide a Fc binding protein suitable for affinity purification. This is achieved with the alkaline stable immunoglobulin (Ig) binding protein comprising one or more Fc binding domains, wherein at least one Fc binding domain comprises, essentially consists, or consists of an amino acid sequence of SEQ ID NOs: 1-6 or 21. In one embodiment the Fc binding protein comprises of 2, 3, 4, 5, or 6 Fc binding domains as defined above linked to each other. In some embodiments, the linker connecting the domains is a peptide linker. In preferred embodiments, the Fc binding protein is conjugated to a solid support.

In some embodiments, the protein is a homo-multimer, while in some embodiments, the protein is a hetero-multimer.

In some embodiments, at least one of the domain of the protein is a derivative of any one of SEQ ID NOs 1-6 or 21, wherein the derivative has an amino acid sequence that is 100% identical to one of SEQ ID NOs: 1-6 or 21 except that it has a deletion of 1, 2, 3, or 4 amino acids within the first 4 amino acids of its N-terminus (position 1, 2, 3, and/or 4) and/or a deletion of 1 or 2 amino acids at the C-terminus (position 57 and/or 58) relative to the one of SEQ ID NOs:1-6 or 21 upon which is based.

In some embodiments, the protein has less than a 15% reduction in binding capacity following an incubation in 0.5 M NaOH for at least 5 hours. For example, the protein may have less than a 10% or less than a 5% reduction in binding capacity following an incubation in 0.5 M NaOH for 6 hours.

In a second aspect, the present invention relates to an affinity separation matrix comprising the Fc binding protein of the first aspect.

In a third aspect, the present invention relates to a use of the Fc binding protein of the first aspect or of the affinity separation matrix of the second aspect for affinity purification of immunoglobulins or proteins comprising a Fc sequence of immunoglobulins.

In a fourth aspect, the present invention relates to a method of affinity purification of immunoglobulins or proteins comprising a Fc sequence of immunoglobulins comprising the steps of (a) providing a liquid containing an immunoglobulin; (b) providing an affinity separation matrix comprising an immobilized Fc binding protein of the first aspect coupled to said affinity separation matrix; (c) contacting said liquid and said affinity separation matrix, wherein said immunoglobulin binds to said immobilized Fc binding protein; and (d) eluting said immunoglobulin from said matrix, thereby obtaining an eluate containing said immunoglobulin. In some embodiments, washing steps can be introduced between steps (c) and (d) of the disclosed method. In some embodiments of the disclosed uses and methods, there is greater than or equal to 95% elution of the protein comprising a Fc sequence at a pH of 3.5 or higher. For example, there is greater than or equal to 98% elution of the protein comprising a Fc sequence at a pH of 3.5 or higher.

In another aspect, the present invention relates to a method of affinity purification of a protein comprising an Fc sequence, the method comprising: (a) contacting an affinity separation matrix comprising at least one Fc binding protein of the first aspect coupled thereto with a solution containing a protein comprising an Fc sequence under conditions that permit binding of said at least one Fc binding protein to said protein comprising an Fc sequence; and (b) eluting the bound protein comprising an Fc sequence from said affinity purification matrix.

This summary of the invention does not necessarily describe all features of the present invention. Other embodiments will become apparent from a review of the ensuing detailed description.

DETAILED DESCRIPTION OF THE INVENTION

Definitions

Figure 1:
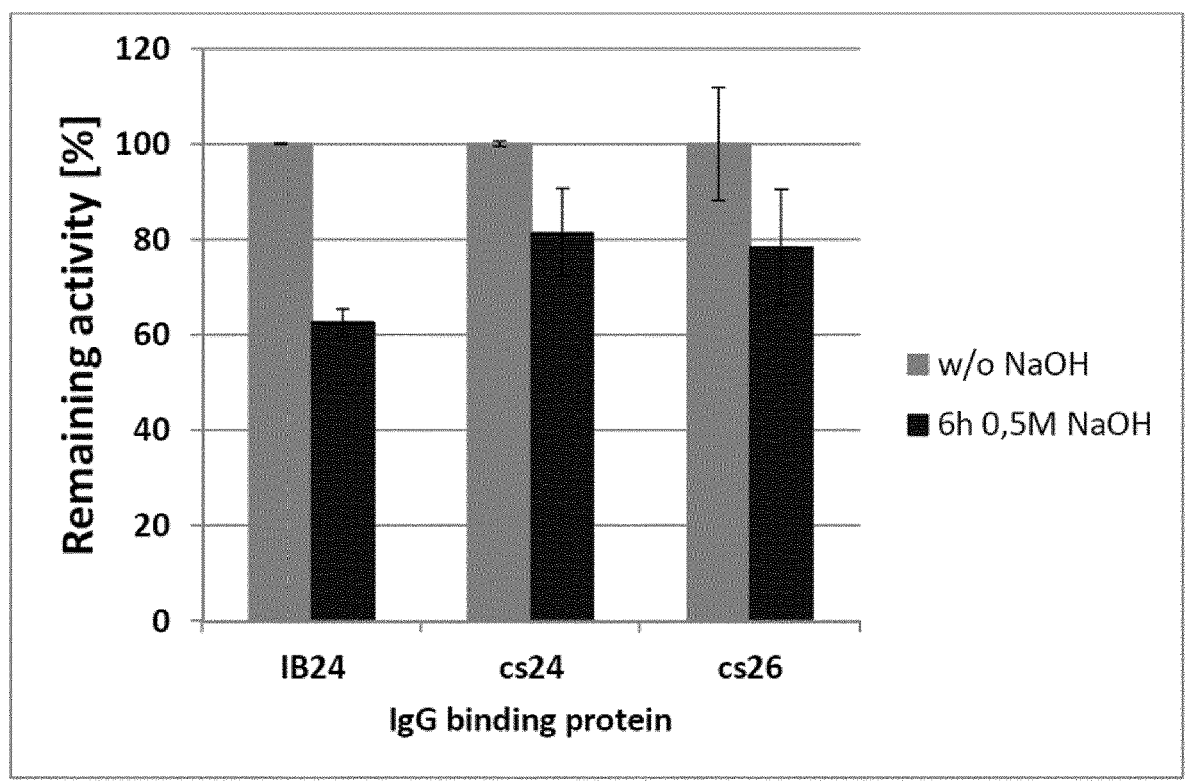
FIG. 1. Analysis of the alkaline stability of different Fc binding domains immobilized on Sepharose 6B matrix after 6 h 0.5 M NaOH treatment. Fc binding domains cs24 (SEQ ID NO: 1) and cs26 (SEQ ID NO: 2) show significantly improved stability at high pH compared to parental domain IB24 (SEQ ID NO: 17).

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are consistent with the definitions provided in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

The term "about", as used herein, encompasses the explicitly recited amounts as well as deviations therefrom of ±10%. More preferably, a deviation 5% is encompassed by the term "about".

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, is a part of this specification.

In the context of the present invention, the term "immunoglobulin-binding protein" is used to describe proteins that are capable to specifically bind to the Fc region of an immunoglobulin. Due to this specific binding to the Fc region, the immunoglobulin-binding proteins of the invention are capable of binding to entire immunoglobulins, to immunoglobulin fragments comprising the Fc region, to fusion proteins comprising a Fc region of an immunoglobulin, and to conjugates comprising a Fc region of an immunoglobulin. While the "immunoglobulin-binding proteins" of the invention herein exhibit specific binding to the Fc region of an immunoglobulin, it is not excluded that "immunoglobulin-binding proteins" can additionally bind with reduced affinity to other regions, such as Fab regions of immunoglobulins.

Throughout this specification, the term "immunoglobulin-binding protein" is often abbreviated as "Fc binding protein" or "Fc-binding protein".

In preferred embodiments of the present invention, the Fc binding protein comprises one or more Fc binding domains.

The term "dissociation constant" or "KD" defines the specific binding affinity. As used herein, the term "KD" (usually measured in "mol/L", sometimes abbreviated as "M") is intended to refer to the dissociation equilibrium constant of the particular interaction between a first protein and a second protein. In the context of the present invention, the term KD is particularly used to describe the binding affinity between an immunoglobulin-binding protein and an immunoglobulin.

A protein of the invention is considered to bind to an immunoglobulin if it has a dissociation constant KD to immunoglobulin of at least 1 µM or less, or preferably 100 nM or less, more preferably 50 nM or less, even more preferably 10 nM or less. For instance, all of the Fc binding domains disclosed in SEQ ID Nos: 1-6 and 21 bind lgG1 with a KD of less than 1 µM or less.

The term "binding" according to the invention preferably relates to a specific binding. "Specific binding" means that a Fc binding protein of the invention binds stronger to an immunoglobulin (or Fc sequence of an immunoglobulin) for which it is specific compared to the binding to another non-immunoglobulin target.

The immunoglobulin as understood herein can include, but is not necessarily limited to, mammalian IgG, such as human IgG-i, human lgG2, human lgG4, mouse IgG-i, mouse lgG2A, mouse lgG2 IgGi, rat lgG2C, goat Igd, goat lgG2, bovine lgG2, guinea pig IgG, rabbit IgG; human IgM, human IgA; and immunoglobulin fragments comprising a Fc region, fusion proteins comprising a Fc region of an immunoglobulin, and conjugates comprising a Fc region of an immunoglobulin. Notably, naturally occurring protein A domains and artificial Fc binding proteins of the invention do not bind to human lgG3.

The terms "protein" and "polypeptide" refer to any linear molecular chain of two or more amino acids linked by peptide bonds and does not refer to a specific length of the product. Thus, "peptides", "protein", "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-translational modifications of the polypeptide, including without limitation glycosylation, acetylation, phosphorylation, amidation, proteolytic cleavage, modification by non-naturally occurring amino acids and similar modifications which are well-known in the art. Thus, Fc binding proteins comprising two or more protein domains also fall under the definition of the term "protein" or "polypeptides".

The term "alkaline stable" or "alkaline stability" or "caustic stable" or "caustic stability" (abbreviated as "cs" herein) refers to the ability of the Fc binding protein of the invention to withstand alkaline conditions without significantly losing the ability to bind to immunoglobulins. The skilled person in this field can easily test alkaline stability by incubating a Fc binding protein with sodium hydroxide solutions, e.g., as described in the Examples, and subsequent testing of the binding activity to immunoglobulin by routine experiments known to someone skilled in the art, for example, by chromatographic approaches.

Fc binding proteins of the invention as well as matrices comprising Fc binding proteins of the invention exhibit an "increased" or "improved" alkaline stability, meaning that the molecules and matrices incorporating said Fc binding proteins are stable under alkaline conditions for an extended period of time relative to the parental Fc binding protein, i.e. do not lose the ability to bind to immunoglobulins or lose the ability to bind to immunoglobulins to a lesser extent than the parental Fc binding protein.

The terms "binding activity" refer to the ability of a Fc binding protein of the invention to bind to immunoglobulin. For example, the binding activity can be determined before and/or after alkaline treatment. The binding activity can be determined for a Fc binding protein or for a Fc binding protein coupled to a matrix, i.e. for an immobilized binding protein. The term "artificial" refers to an object that is not naturally occurring, i.e. the term refers to an object that has been produced or modified by man. For example, a polypeptide or polynucleotide sequence that has been generated by man (e.g., for example in a laboratory by genetic engineering, by shuffling methods, or by chemical reactions, etc.) or intentionally modified is artificial.

The term "parental" in the term "parental Fc binding protein" or "parental Fc binding domain" as used herein refers to a Fc binding protein that is subsequently modified to generate a variant of said parental protein or domain. Such parent proteins or domains may be an artificial Fc binding domain, as disclosed herein as IB24 (SEQ ID NO: 17) or IB26 (SEQ ID NO: 18).

The term "conjugate" as used herein relates to a molecule comprising or essentially consisting of at least a first protein attached chemically to other substances such as to a second protein or a non-proteinaceous moiety.

The term "substitution" or "amino acid substitution" refers to an exchange of an amino acid at a particular position in a parent polypeptide sequence by another amino acid. Given the known genetic code, and recombinant and synthetic DNA techniques, the skilled scientist can readily construct DNAs encoding the amino acid variants.

The term "amino acid sequence identity" refers to a quantitative comparison of the identity (or differences) of the amino acid sequences of two or more proteins. "Percent (%) amino acid sequence identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity.

To determine the sequence identity, the sequence of a query protein is aligned to the sequence of a reference protein. Methods for alignment are well-known in the art.

The term "fused" means that the components are linked by peptide bonds, either directly or via peptide linkers.

The term "fusion protein" relates to a protein comprising at least a first protein joined genetically to at least a second protein. A fusion protein is created through joining of two or more genes that originally coded for separate proteins. Thus, a fusion protein may comprise a multimer of identical or different proteins which are expressed as a single, linear polypeptide As used herein, the term "linker" refers in its broadest meaning to a molecule that covalently joins at least two other molecules. In typical embodiments of the present invention, a "linker" is to be understood as a moiety that connects a Fc binding domain with at least one further Fc binding domain, i.e. a moiety linking two protein domains to each other to generate a multimer. In preferred embodiments, the "linker" is a peptide linker, i.e. the moiety linking the two protein domains is one single amino acid or a peptide comprising two or more amino acids.

The term "chromatography" refers to separation technologies which employ a mobile phase and a stationary phase to separate one type of molecules (e.g., immunoglobulins) from other molecules (e.g., contaminants) in the sample. The liquid mobile phase contains a mixture of molecules and transports these across or through a stationary phase (such as a solid matrix). Due to the differential interaction of the different molecules in the mobile phase with the stationary phase, molecules in the mobile phase can be separated.

The term "affinity chromatography" refers to a specific mode of chromatography in which a ligand coupled to a stationary phase interacts with a molecule (i.e. immunoglobulin) in the mobile phase (the sample) i.e. the ligand has a specific binding affinity for the molecule to be purified. As understood in the context of the invention, affinity chromatography involves the addition of a sample containing an immunoglobulin to a stationary phase which comprises a chromatography ligand, such as a Fc binding protein of the invention.

The terms "solid support" or "solid matrix" are used interchangeably for the stationary phase.

The terms "affinity matrix" or "affinity separation matrix" or "affinity chromatography matrix", as used interchangeably herein, refer to a matrix, e.g., a chromatographic matrix, onto which an affinity ligand e.g., a Fc binding protein of the invention is attached. The ligand (e.g., Fc binding protein) is capable of specific binding to a molecule of interest (e.g., an immunoglobulin or a Fc-containing protein) which is to be purified or removed from a mixture.

The term "affinity purification" as used herein refers to a method of purifying immunoglobulins or Fc-containing proteins from a liquid by binding the immunoglobulins or Fc-containing proteins to a Fc binding protein that is immobilized to a matrix. Thereby, all other components of the mixture except immunoglobulins or Fc-containing proteins are removed. In a further step, the bound immunoglobulins or Fc-containing proteins can be eluted in purified form.

Embodiments of the Invention

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

In a first aspect the present invention is directed to a Fc binding protein, comprising one or more Fc binding domains, wherein at least one Fc binding domain comprises, consists essentially of, or consists of an amino acid sequence of SEQ ID NOs: 1-6 or 21. One advantage of the disclosed Fc binding domains and proteins comprising said domains is that they remain stable even after alkaline treatment, in particular as compared to parent proteins and other known Fc binding proteins. For example, in some embodiments, the disclosed Fc binding domains and proteins comprising said domains may be greater than at least about 15%, at least about 20%, at least about 25%, or at least about 30% more stable than Protein A domain C after being exposed to alkaline conditions. In other words, the disclosed Fc binding domains have less reduction of binding capacity following ≥5 hour incubation time with 0.5 M NaOH when compared to Protein A domain C. Thus, in some embodiments, the disclosed Fc proteins have less than a 20% reduction in binding capacity following an incubation in 0.5 M NaOH for at least 5 hours (e.g., 6 hours). In some embodiments, the reduction in binding capacity of the disclosed Fc proteins following an incubation in 0.5 M NaOH for at least 5 hours may be less than about 15%, less than about 10%, or less than about 5%.

All Fc binding proteins of the invention bind to Immunoglobulin with a dissociation constant KD below 1 µM, or preferably below 100 nM, or even more preferably 10 nM or less. Methods for determining binding affinities of Fc binding proteins or domains, i.e. for determining the dissociation constant KD, are known to a person of ordinary skill in the art and can be selected for instance from the following methods known in the art: Surface Plasmon Resonance (SPR) based technology, Bio-layer interferometry (BLI), enzyme-linked immunosorbent assay (ELISA), flow cytometry, isothermal titration calorimetry (ITC), analytical ultracentrifugation, radioimmunoassay (RIA or IRMA) and enhanced chemiluminescence (ECL). Some of the methods are described further in the Examples. Typically, the dissociation constant KD is determined at 20° C., 25° C., or 30° C. If not specifically indicated otherwise, the KD values recited herein are determined at 22° C.+/−3° C. by surface plasmon resonance. In an embodiment of the first aspect, the Fc binding protein has a dissociation constant KD to human Igd in the range between 0.1 nM and 100 nM, preferably between 0.1 nM and 10 nM.

As shown in the examples below, surprisingly and unexpected the Fc binding proteins of the invention were found to bind to IgG even after prolonged alkaline treatment. In some embodiments, the Fc binding proteins of the invention exhibit an improved alkaline stability as compared to a corresponding parental protein. The alkaline stability of the Fc binding protein is determined by comparing the loss in IgG-binding activity of the Fc binding protein after 6 h incubation in 0.5 M NaOH, as compared to the loss in IgG-binding activity of the corresponding parental protein after 6 h incubation in 0.5 M NaOH. The loss of binding activity is determined by comparing binding activity before and after 0.5 M NaOH incubation for 6 hours.

Figure 2:
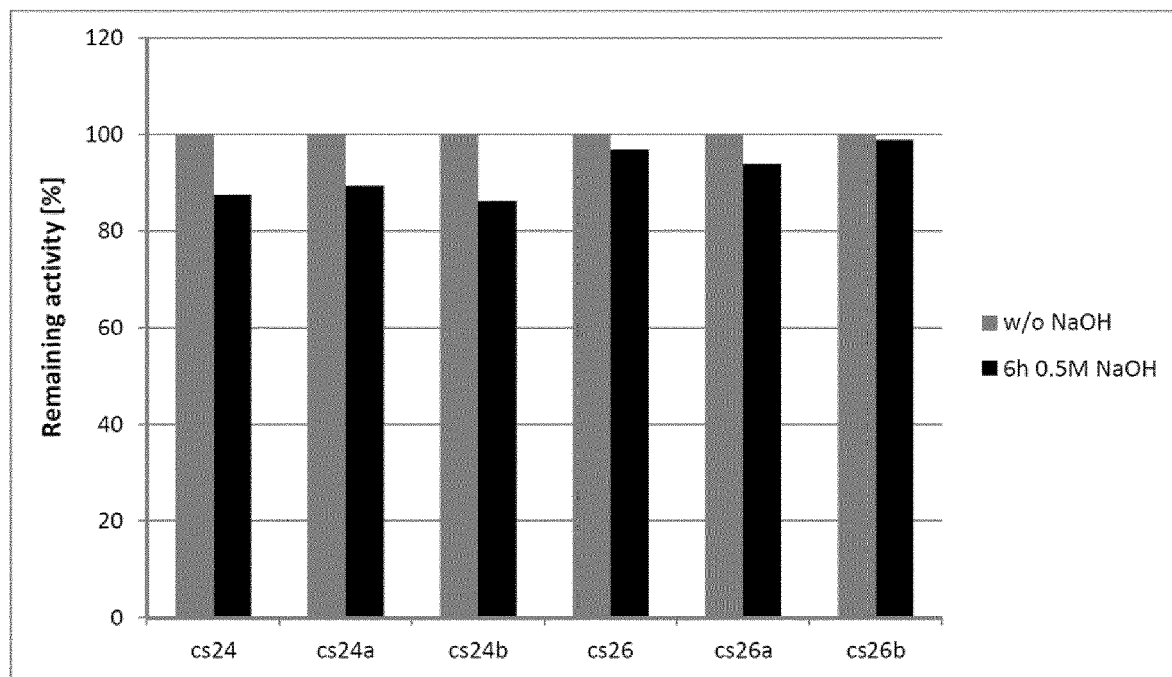
FIG. 2. Analysis of the activity of Fc binding domains immobilized on Praesto™ Pure 45 matrix pH 9.5 after incubation for 6 h at 0.5 M NaOH. Fc binding domains cs24 (SEQ ID NO: 1), cs24a (SEQ ID NO: 3), cs24b (SEQ ID NO: 5), cs26 (SEQ ID NO: 2), cs26a (SEQ ID NO: 4), and cs26b (SEQ ID NO: 6).

As shown by the comparative data in FIG. 1, the IgG binding activity of cs24 and cs26 is increased by at least about 30% compared to IB24. This is an unexpected and advantageous property of cs24 and cs26 as compared to parental IB24. FIG. 2 shows that all Fc binding proteins of SEQ ID NOs: 1-6 have at least 87.6% binding activity remaining activity after 6 h incubation at 0.5 M NaOH In one embodiment of the invention, the Fc binding protein comprises 2, 3, 4, 5, or 6 Fc binding domains linked to each other, i.e. the Fc binding protein can be a monomer, dimer, trimer, tetramer, pentamer, or hexamer.

In some embodiments, the domains are selected from the group consisting of SEQ ID NOs: 1-6 and 21. In other embodiments, the domains are derivatives of SEQ ID NOs: 1-6 or 21 and further wherein each derivative has an amino acid sequence that is 100% identical to one of SEQ ID NOs: 1-6 except that it has a deletion of 1, 2, 3, or 4 amino acids within the first 4 amino acids of its N-terminus and/or a deletion of 1 or 2 amino acids at the C-terminus (position 57 and/or 58) relative to the one of SEQ ID NOs:1-6 or 21 upon which it is based (see, for example, SEQ ID NOs: 7-16).

Multimers of the invention are fusion proteins generated artificially, generally by recombinant DNA technology well-known to a skilled person. Fc binding proteins of the invention may be prepared by any of the many conventional and well-known techniques such as plain organic synthetic strategies, solid phase-assisted synthesis techniques or by commercially available automated synthesizers.

In some embodiments of the first aspect, the multimer is a homo-multimer, e.g., the amino acid sequences of all Fc binding domains of the Fc binding protein are identical.

In some embodiments of the first aspect, the multimer is a hetero-multimer, e.g., at least one Fc binding domain has a different amino acid sequence than the other Fc binding domains within the Fc binding protein.

In some embodiments of the first aspect, the Fc binding domains are directly linked to each other. In other embodiments, the one or more Fc binding domains are linked to each other with one or more linkers. Preferred in these typical embodiments are peptide linkers. This means that the peptide linker is an amino acid sequence that connects a first Fc binding domain with a second Fc binding domain. The peptide linker is connected to the first Fc binding domain and to the second Fc binding domain by a peptide bond between the C-terminal and N-terminal ends of the domains, thereby generating a single, linear polypeptide chain. The length and composition of a linker may vary between at least one and up to about 30 amino acids. More specifically, a peptide linker has a length of between 1 and 30 amino acids; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 amino acids. It is preferred that the amino acid sequence of the peptide linker is stable against caustic conditions and proteases. Linkers should not destabilize the conformation of the domains in the Fc binding protein. Well-known are linkers comprising small amino acids such as glycine and serine. The linkers can be glycine-rich (e.g., more than 50% of the residues in the linker can be glycine residues). Also preferred are linkers that comprise further amino acids. Other embodiments of the invention comprise linkers consisting of alanine, proline, and serine. Other linkers for the fusion of proteins are known in the art and can be used.

In some embodiments, the Fc binding protein further comprises an attachment site for covalent attachment to a solid phase (matrix). Preferably, the attachment site is specific to provide a site-specific attachment of the Fc binding protein to the solid phase. Specific attachment sites comprise natural amino acids, such as cysteine or lysine, which enable specific chemical reactions with a reactive group of the solid phase or a linker between the solid phase and the protein, for example selected from N-hydroxysuccinimide, iodacetamide, maleimide, epoxy, or alkene groups. The attachment site may be directly at the C- or N-terminal end of the Fc binding protein or there may be a linker between the N- or C-terminus and the coupling site, preferably a peptide linker. In some embodiments of the invention, the Fc binding protein may comprise a short N- or C-terminal peptide sequence of 3-20 amino acids, preferably 4-10 amino acids, with a terminal cysteine. Amino acids for a C-terminal attachment site may be preferably selected from proline, alanine, and serine, for example, ASPAPSAPSAC (SEQ ID NO: 19), with a single cysteine at the C-terminal end for coupling. In another embodiment, amino acids for a C-terminal attachment site may be preferably selected from glycine and serine, for example, GGGSC (SEQ ID NO: 22), with a single cysteine at the C-terminal end for coupling.

An advantage of having a C-terminal cysteine is that coupling of the Fc binding protein can be achieved through reaction of the cysteine thiol with an electrophilic group on a support resulting in a thioether bridge coupling. This provides excellent mobility of the coupled protein which provides increased binding capacity.

In a second aspect the, present invention is directed to an affinity separation matrix, comprising an Fc binding protein of the first aspect.

In preferred embodiments of the second aspect, the affinity separation matrix is a solid support. The affinity separation matrix comprises at least one Fc binding protein comprising at least one Fc binding domain comprising any one of SEQ ID NOs: 1-6 or 21.

This matrix comprising the Fc binding protein of the invention is useful for separation, for example for chromatographic separation, of immunoglobulins and other Fc-containing proteins, such as immunoglobulin variants comprising the Fc region, fusion proteins comprising a Fc region of an immunoglobulin, and conjugates comprising a Fc region of an immunoglobulin. An affinity matrix is useful for separation of immunoglobulins and should retain the Fc binding property even after highly alkaline conditions as applied during cleaning processes. Such cleaning of matrices is essential for long-term repeated use of matrices.

Solid support matrices for affinity chromatography are known in the art and include for example but are not limited to, agarose and stabilized derivatives of agarose (e.g., Sepharose 6B, Praesto™Pure; CaptivA®, Mabselect®, PROTEIN A Sepharose Fast Flow), cellulose or derivatives of cellulose, controlled pore glass (e.g., ProSep® vA resin), monolith (e.g., CIM® monoliths), silica, zirconium oxide (e.g., CM Zirconia or CPG®), titanium oxide, or synthetic polymers (e.g., polystyrene such as Poros 50A or Poros MabCapture® A resin, polyvinylether, polyvinyl alcohol, polyhydroxyalkyl acrylates, polyhydroxyalkyl methacrylates, polyacrylamides, polymethacrylamides etc) and hydrogels of various compositions. In certain embodiments the support comprises a polyhydroxy polymer, such as a polysaccharide. Examples of polysaccharides suitable for supports include but are not limited to agar, agarose, dextran, starch, cellulose, pullulan, etc, and stabilized variants of these.

The formats for solid support matrices can be of any suitable well-known kind. Such solid support matrix for coupling the Fc binding protein of the invention might comprise, for example, one of the following: columns, capillaries, particles, membranes, filters, monoliths, fibers, pads, gels, slides, plates, cassettes, or any other format commonly used in chromatography and known to someone skilled in the art.

In one embodiment, the matrix is comprised of substantially spherical particles, also known as beads, for example Sepharose or Agarose beads. Suitable particle sizes may be in the diameter range of 5-500 μm, such as 10-100 μm, e.g., 20-80 μm. Matrices in particle form can be used as a packed bed or in a suspended form including expanded beds.

In an alternative embodiment, the solid support matrix is a membrane, for example a hydrogel membrane. In some embodiments, the affinity purification involves a membrane as matrix to which the Fc binding protein of the first aspect is covalently bound. The solid support can also be in the form of a membrane in a cartridge.

In some embodiments, the affinity purification involves a chromatography column containing a solid support matrix to which the Fc binding protein of the first aspect is covalently bound.

The Fc binding protein of the invention may be attached to a suitable solid support matrix via conventional coupling techniques utilising, e.g., amino-, sulfhydroxy-, and/or carboxy-groups present in the Fc binding protein of the invention. The coupling may be carried out via a nitrogen, oxygen, or sulphur atom of the Fc binding protein. Preferably, amino acids comprised in an N- or C-terminal peptide linker comprise said nitrogen, oxygen, or sulphur atom.

The Fc binding proteins may be coupled to the support matrix directly or indirectly via a spacer element to provide an appropriate distance between the matrix surface and the Fc binding protein of the invention which improves the availability of the Fc binding protein and facilitates the chemical coupling of the Fc binding protein of the invention to the support.

Methods for immobilization of protein ligands to solid supports are well-known in this field and easily performed by the skilled person in this field using standard techniques and equipment.

Depending on the Fc binding protein and on the specific conditions, the coupling may be a multipoint coupling, for example via several lysines, or a single point coupling, for example via cysteine.

In a third aspect, the present invention is directed to the use of the Fc binding protein of the first aspect or an affinity matrix of the second aspect for affinity purification of immunoglobulins or variants thereof, i.e. the Fc binding protein of the invention is used for affinity chromatography. In some embodiments, the Fc binding protein of the invention is immobilized onto a solid support as described in the second aspect of the invention.

In a fourth aspect the present invention is directed to a method for affinity purification of a protein comprising an Fc sequence, the method comprising:

(a) providing a solution that contains a protein comprising an Fc sequence;
(b) providing an affinity separation matrix comprising at least one Fc binding protein of the invention thereto;
(c) contacting said affinity separation matrix with the solution under conditions that permit specific binding of the at least one Fc binding protein of the invention to a protein comprising an Fc sequence; and
(d) eluting said protein comprising an Fc sequence from said affinity purification matrix, and
(e) optionally comprising washing the affinity matrix between step (c) and (d).

For the purposes of the disclosed uses and methods, the protein comprising an Fc sequence is an immunoglobulin molecule or a fragment or derivative thereof that comprises an Fc sequence, consistent with the definitions provided herein.

Affinity separation matrixes suitable for the disclosed uses and methods are those matrixes according to the embodiments described above and as known to someone skilled in the art.

In some embodiments of the fourth aspect, the elution of the immunoglobulin from the matrix in step (d) is effected through a change in pH and/or a change in salt concentration. Any suitable solution used for elution from Protein A media can be used, for example by a solution with pH 5 or lower, or by a solution with pH 11 or higher.

In some embodiments, a further step (f) for efficient cleaning the affinity matrix is added, preferably by using an alkaline liquid, for example, with pH of 13-14. In certain embodiments, the cleaning liquid comprises 0.1-1.0 M NaOH or KOH, preferably 0.25-0.5 M NaOH or KOH. Due to the high alkaline stability of the Fc binding proteins of the invention, such strong alkaline solution can be used for cleaning purposes.

In some embodiments, the affinity matrix can be re-used at least 10 times, at least 20 times, at least 30 times, at least 40 times, at least 50 times, at least 60 times, at least 70 times, at least 80 times, at least 90 times, or at least 100 times, due to a repetition of steps (a) to (e), optionally (a) to (f) can be repeated at least 10 times, at least 20 times, at least 30 times, at least 40 times, at least 50 times, at least 60 times, at least 70 times, at least 80 times, at least 90 times, or at least 100 times.

In general, suitable conditions for performing the method of affinity purification are well known to someone skilled in the art. In some embodiments, the disclosed uses or methods of affinity purification comprising the disclosed Fc binding domains may provide elution of at least about 95%, at least about 96%, at least about 97%, at least about 98%, at least about 99%, or at least about 100% of Fc containing proteins at a pH of greater than or equal to 3.5 (e.g., about 4.0, about 4.5, about 5.0, about 5.5, about 6.0, or about 6.5). In some embodiments, the elution profile of the disclosed Fc binding domains is superior to Protein A domain C.

In a fifth aspect, the present invention is directed to a nucleic acid molecule, preferably an isolated nucleic acid molecule, encoding a Fc binding protein or Fc binding domain of any embodiment disclosed above. In one embodiment, the present invention is directed to a vector comprising the nucleic acid molecule. A vector means any molecule or entity (e.g., nucleic acid, plasmid, bacteriophage or virus) that can be used to transfer protein coding information into a host cell. In one embodiment, the vector is an expression vector.

In a sixth aspect, the present invention is directed to an expression system which comprises a nucleic acid or a vector as disclosed above, for example a prokaryotic host cell, for example *E. coli*, or a eukaryotic host, for example yeast *Saccharomyces cerevisiae* or *Pichia pastoris* or mammalian cells such as CHO cells.

In a seventh aspect, the present invention is directed to a method for the production of an Fc binding protein of the first aspect, comprising the step(s): (a) culturing the host cell of the sixth aspect under suitable conditions for the expression of the binding protein in order to obtain said Fc binding protein; and (b) optionally isolating said Fc binding protein.

Suitable conditions for culturing a prokaryotic or eukaryotic host are well-known to the person skilled in the art.

Fc binding molecules of the invention may be prepared by any of the many conventional and well-known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

One embodiment of the present invention is directed to a method for the preparation of an alkaline-stable Fc binding protein comprising at least one Fc binding domain comprising a sequence of any one of SEQ ID NOs: 1-6 or 21, said method comprising the following steps: (a) preparing a nucleic acid encoding a Fc binding protein as defined above; (b) introducing said nucleic acid into an expression vector; (c) introducing said expression vector into a host cell; (d) cultivating the host cell; (e) subjecting the host cell to culturing conditions under which a Fc binding protein is expressed, thereby (e) producing a Fc binding protein as described above; optionally (f) isolating the protein produced in step (e); and (g) optionally conjugating the protein to solid matrices as described above.

In a further embodiment of the present invention the production of the Fc binding protein is performed by cell-free in vitro transcription/translation.

EXAMPLES

The following Examples are provided for further illustration of the invention. The invention, however, is not limited thereto, and the following Examples merely show the practicability of the invention on the basis of the above description.

Example 1. Generation of Parental Fc Binding Proteins of the Invention

Parental proteins SEQ ID NO: 17 or SEQ ID NO: 18 were initially generated by a shuffling process of naturally occurring Protein A domains. In more detail, the shuffling process as understood herein is an assembly process resulting in artificial amino acid sequences starting from a set of non-identical known amino acid sequences. The shuffling process comprised the following steps: a) providing sequences of five naturally occurring Protein A domains E, B, D, A, and C, and Protein A variant domain Z; b) alignment of said sequences; c) statistical fragmentation in silico to identify subsequences that were recombined, and then d) assembly of new, artificial sequences of the various fragments to produce a mosaic product, i.e. a novel amino acid sequence. The fragments generated in step c) were of any length, e.g., if the fragmented parent sequence had a length of n, the fragments was of length 1 to n–1.

The relative positions of the amino acids in the mosaic products were maintained with respect to the starting amino acid sequences. At least 90% of positions Q9, Q10, A12, F13, Y14, L17, P20, L22, Q26, R27, F30, I31, Q32, S33, L34, K35, D36, D37, P38, S39, S41, L45, E47, A48, K50, L51, Q55, A56, P57 are identical between the artificial amino acid sequences of parental "shuffled" proteins IB24 and IB26, and naturally occurring Protein A domains or Protein A domain variants, provided that position 4 of IB24 and IB26 is Q. The overall amino acid sequence of parental proteins IB24 or IB26 is artificial in that it is not more than about 85% identical to the overall amino acid sequence of any of the naturally occurring Protein A domains or domain Z (for example, IB24 or IB26 are only 77% identical to domain B). After the initial artificial proteins was generated, the protein was further modified by site-specific randomization of the amino acid sequence to further modify the binding properties. The further modifications were introduced by site-saturation mutagenesis of individual amino acid residues.

Genes for IB24 and IB26 were synthesized and cloned into an *E. coli* expression vector using standard methods known to a skilled person. DNA sequencing was used to verify the correct sequence of inserted fragments.

To generate multimeric Fc binding proteins comprising more than one binding domain, 2, 3, 4, 5, or 6 Fc binding domains were genetically fused.

For specific membrane attachment and purification, a short peptide amino acid sequence with C-terminal Cys (SEQ ID NO: 19) and optionally a strep-tag (SEQ ID NO: 20) were added to the C-terminus of the Fc binding proteins.

Example 2. Mutagenesis of Fc Binding Proteins

For site-directed mutagenesis, the Q5® site-directed Mutagenesis Kit (NEB; Cat. No. E0554S) was used according to the manufacturer's instructions. A combination of several point mutations was generated by GeneArt™ Strings™ synthesis (Thermo Fisher Scientific). The Strings DNA fragments corresponded to a purified PCR product and were cloned into a derivate of a pET28a vector. Ligation products were transformed into *E. coli* XL2-blue cells via electroporation. Single colonies were screened by PCR to identify constructs containing inserts of the right size. DNA sequencing was used to verify the correct sequences.

Example 3. Expression of Fc Binding Proteins

BL21 (DE3) competent cells were transformed with an expression plasmid encoding Fc binding proteins. Cells were spread onto selective agar plates (Kanamycin) and incubated overnight at 37° C. Precultures were inoculated from single colony in 100 ml 2×YT medium and cultured for 16 hours at 37° C. at 160 rpm in a conventional orbital shaker in baffled 1 L Erlenmeyer flasks supplemented with 150 μg ml Kanamycin without lactose and antifoam. The OD600 readout should be in the range of 6-12. Main culture was inoculated from previous overnight culture with an adjusted start-OD600 of 0.5 in 400 ml superrich medium (modified H15 medium 2% Glucose, 5% Yeast extract, 0.89% Glycerol, 0.76% Lactose, 250 mM MOPS, 202 mM TRIS, pH 7.4, Antifoam SE15) in 1 L thick-walled Erlenmeyer flasks that was supplemented with 150 μg ml Kanamycin. Cultures were transferred to a resonant acoustic mixer (RAMbio) and incubated at 37° C. with 20×g. Aeration was facilitated by Oxy-Pump stoppers. Recombinant protein expression was induced by metabolizing glucose and subsequently allowing lactose to enter the cells. At predefined time points OD600 was measured, samples adjusted to 5/OD600 were withdrawn, pelleted and frozen at −20° C. Cells were grown overnight for approx. 24 hours to reach a final OD600 of about 45-60. To collect biomass cells were centrifuged at 16000×g for 10 min at 20° C. Pellets were weighed (wet weight) and pH was measured in the supernatant. Cells were stored at −20° C. before processing.

Example 4: SDS-PAGE Analysis of Expression and Solubility of Fc Binding Proteins Samples taken during fermentation were resuspended in 300 μl extraction buffer (PBS supplemented with 0.2 mg/ml Lysozyme, 0.5× BugBuster, 7.5 mM MgSO4, 40 U Benzonase) and solubilized by agitation in a thermomixer at 700 rpm, rt for 15 min. Soluble proteins were separated from insoluble proteins by centrifugation (16000×g, 2 min, rt). Supernatant was withdrawn (soluble fraction) and the pellet (insoluble fraction) was resuspended in equivalent amount of urea buffer (8 M urea, 0.2 M Tris, 2 mM EDTA, pH 8.5). 50 μl were taken both from the soluble and insoluble fraction, and 12 μl 5× sample buffer as well as 5 μl 0.5 M DTT were added. Samples were boiled at 95° C. for 5 min. Finally, 8 μl of those samples were applied to NuPage Novex 4-12% Bis-Tris SDS gels which were run in accordance to the manufacturer's recommendations and stained with Coomassie. High level expression of Fc binding proteins was found under optimized conditions within the chosen period of time (data not shown). All expressed Fc binding proteins were soluble to more than 95% according to SDS-PAGE.

Example 5: Purification of Fc Binding Proteins

Fc binding proteins were expressed in the soluble fraction of *£. co//* with a C-terminal StrepTagll (SEQ ID NO: 20). The cells were lysed by two freeze/thaw cycles and the purification step was performed with Strep-Tactin®-resin according to the manufacturer's instructions (IBA, Goettingen, Germany). To avoid disulfide formation the buffers were supplemented with 1 mM DTT.

Alternatively, Fc binding proteins were expressed in the soluble fraction of *E. coli* with a C-terminal StrepTagll. The cells were resuspended in cell disruption buffer and lysed by a constant cell disruption system (Unit F8B, Holly Farm Business Park) at 1 kbar for two cycles. Purification step was performed with Strep-TactinYesin (IBA, Goettingen, Germany) and additional gel filtration (Superdex 75 16/60; GE Healthcare) using an AKTAxpress system (Ge Healthcare) according to the manufacturer's instructions. To avoid disulfide formation buffers for Strep-Tactin-purification were supplemented with 1 mM DTT and citrate-buffer (20 mM Citrat, 150 mM NaCl, pH 6.0) was used as running buffer for gel filtration.

Example 6. The Fc Binding Proteins Bind to IgG with High Affinities (as Determined with Surface Plasmon Resonance Experiments)

A CM5 sensor chip (GE Healthcare) was equilibrated with SPR running buffer. Surface-exposed carboxylic groups were activated by passing a mixture of EDC and NHS to yield reactive ester groups. 700-1500 RU on-ligand were immobilized on a flow cell, off-ligand was immobilized on another flow cell. Injection of ethanolamine after ligand immobilization, ethanolamin and 10 nM Glycin pH 2.0 are injected to remove non-covalently bound Fc binding protein. Upon ligand binding, protein analyte was accumulated on the surface increasing the refractive index. This change in the refractive index was measured in real time and plotted as response or resonance units (RU) versus time. The analytes were applied to the chip in serial dilutions with a suitable flow rate (μl/min). After each run, the chip surface was regenerated with regeneration buffer and equilibrated with running buffer. The control samples were applied to the matrix. Regeneration and re-equilibration were performed as previously mentioned. Binding studies were carried out by the use of the Biacore® 3000 (GE Healthcare) at 25° C.; data evaluation was operated via the BIAevaluation 3.0 software, provided by the manufacturer, by the use of the Langmuir 1:1 model (R1=0). Evaluated dissociation constants (KD) were standardized against off-target. The binding affinities of SEQ ID NO: 1 and SEQ ID NO: 2 for human IgGi (Cetuximab), human lgG2 (Panitumomab), and human lgG4 (Natalizumab) are shown in Table 1.

TABLE 1

$K_D$ values of Fc binding proteins of the invention

| CID | Exchange | SE-HPLC [%] | Rp-HPLC [%] | KD vs. IgG 2 [nM] | KD vs. IgG 2 [nM] | KD vs. IgG 2 [nM] |
|---|---|---|---|---|---|---|
| Wt C-domain | | 100 | 100 | 7.2 | 129 | 8.0 |
| CS24 | | 100 | 100 | 17.2 | 101 | 12.4 |
| CS24 | Q9H | 100 | 100 | 617 | 6720 | 403 |
| CS24 | D36H | 100 | 100 | 16.1 | 169 | 10.6 |
| CS26 | | 100 | 100 | 18.4 | 193 | 10.9 |
| CS26 | Q9H | 100 | 100 | 668 | 3320 | 265 |
| CS26 | D36H | 100 | 100 | 14.4 | 153 | 11.2 |

Example 7. Alkaline Stability of Fc Binding Proteins Coupled to Sepharose 6B Matrix Purified Fc binding proteins were coupled to epoxy-activated matrix (Sepharose 6B, GE; Cat. No. 17-0480-01) according to the manufacturer's instructions (coupling conditions: pH 9.0 overnight, blocking for 5 h with ethanolamine). Cetuximab was used as IgGi sample (5 mg; 1 mg/ml matrix). Cetuximab was applied in saturated amounts to the matrix comprising immobilized Fc binding protein. The matrix was washed with 100 mM glycine buffer, pH 2.5 to elute Cetuximab that was bound to the immobilized IgG-binding protein. The concentration of the eluted IgG was measured by BLI (quantification with Protein A Octet-sensors and Cetuximab as standard) in order to determine the binding activity of the Fc binding proteins. Columns were incubated with 0.5 M NaOH for 6 h at room temperature (22° C.+/−3° C.). The IgG binding activity of the immobilized proteins was analyzed before and after incubation with 0.5 M NaOH for 6 h. The IgG binding activity of immobilized proteins before NaOH treatment was defined as 100%.

FIG. 1 shows that the activity of Fc binding proteins SEQ ID NO: 1 and SEQ ID NO: 2 was higher compared to the activity of the parental protein IB24 (parental IB26 is comparable to parental IB24; data not shown). Both Fc binding proteins SEQ ID NO: 1 and SEQ ID NO: 2 showed about at least 30% higher IgG binding activity compared to the parental protein IB24 after incubation for 6 h at 0.5 M NaOH. Thus, the Fc binding proteins of the invention show significantly improved stability at high pH, compared to a parental protein.

Example 8. Alkaline Stability of Fc Binding Proteins Coupled to Agarose-Based Chromatography Beads Praesto™ Pure45

Purified Fc binding proteins were coupled to agarose-based chromatography beads (Praesto™ Pure45, Purolite; Cat. No. PR01262-166) according to the manufacturer's instructions (coupling conditions: pH 9.5, 3 hours, 35° C., blocking overnight with ethanolamine). Polyclonal human IgG Gammanorm® (Ocatpharm) was used as IgG sample (conc. 2.2 mg/ml). Polyclonal hIgG sample was applied in saturated amounts to the matrix comprising immobilized Fc binding protein. The matrix was washed with 100 mM Citrate buffer, pH 2.0 to elute hIgG that was bound to the immobilized Fc binding protein. Dynamic binding capacity was determined by the mass of injected hIgG at 10% breakthrough at 6 min residence time. Columns were incubated with 0.5 M NaOH for 6 h at room temperature (22° C.+/−3° C.). The IgG binding activity of the immobilized proteins was analyzed before and after incubation with 0.5 M NaOH for 6 h. The IgG binding activity of immobilized proteins before NaOH treatment was defined as 100%.

Figure 3:
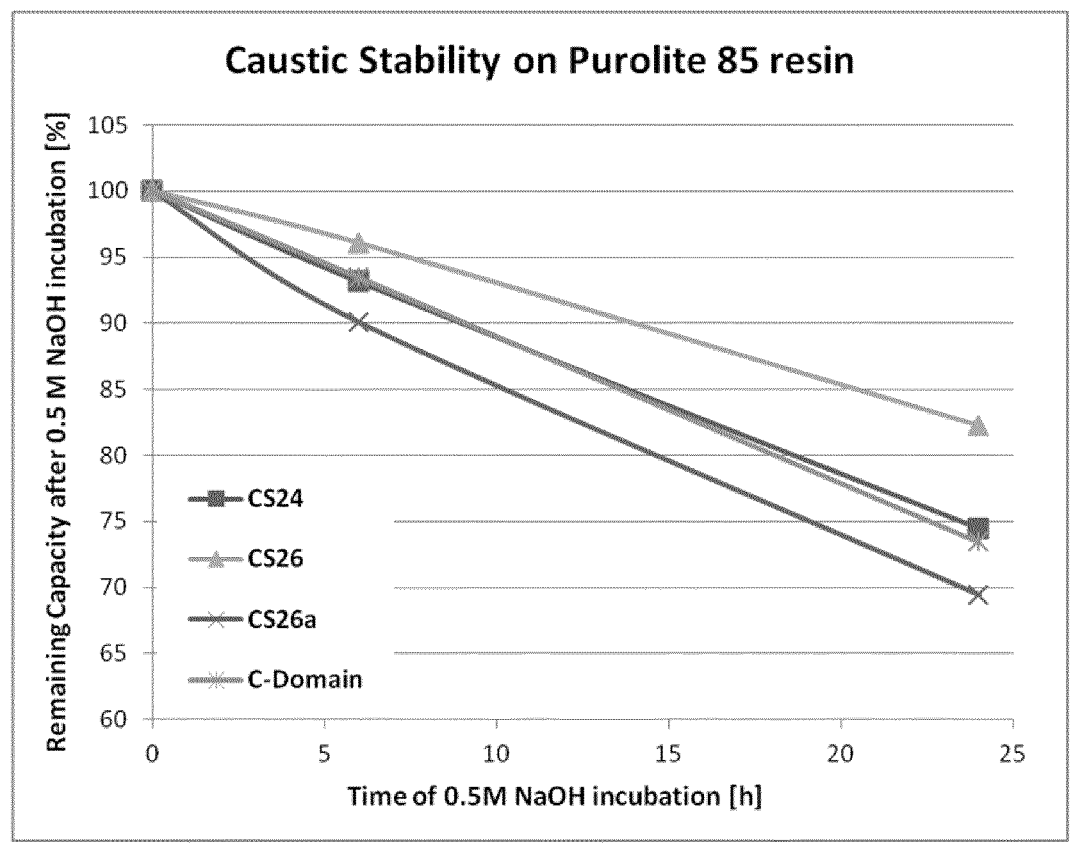
FIG. 3. Analysis of the activity of Fc binding domains immobilized on Praesto™ Pure 85 matrix (panel A) and on Praesto™ Pure 45 matrix (panel B) at pH 9.5 after incubation for 6 h, and 24 h (panel A), and 6 h, 24 h, and 36 h (panel B) at 0.5 M NaOH. Fc binding domains cs24 (SEQ ID NO: 1), cs24a (SEQ ID NO: 3), cs24b (SEQ ID NO: 5), cs26 (SEQ ID NO: 2), cs26a (SEQ ID NO: 4), and cs26b (SEQ ID NO: 6), compared to wildtype domain C.
Figure 3:
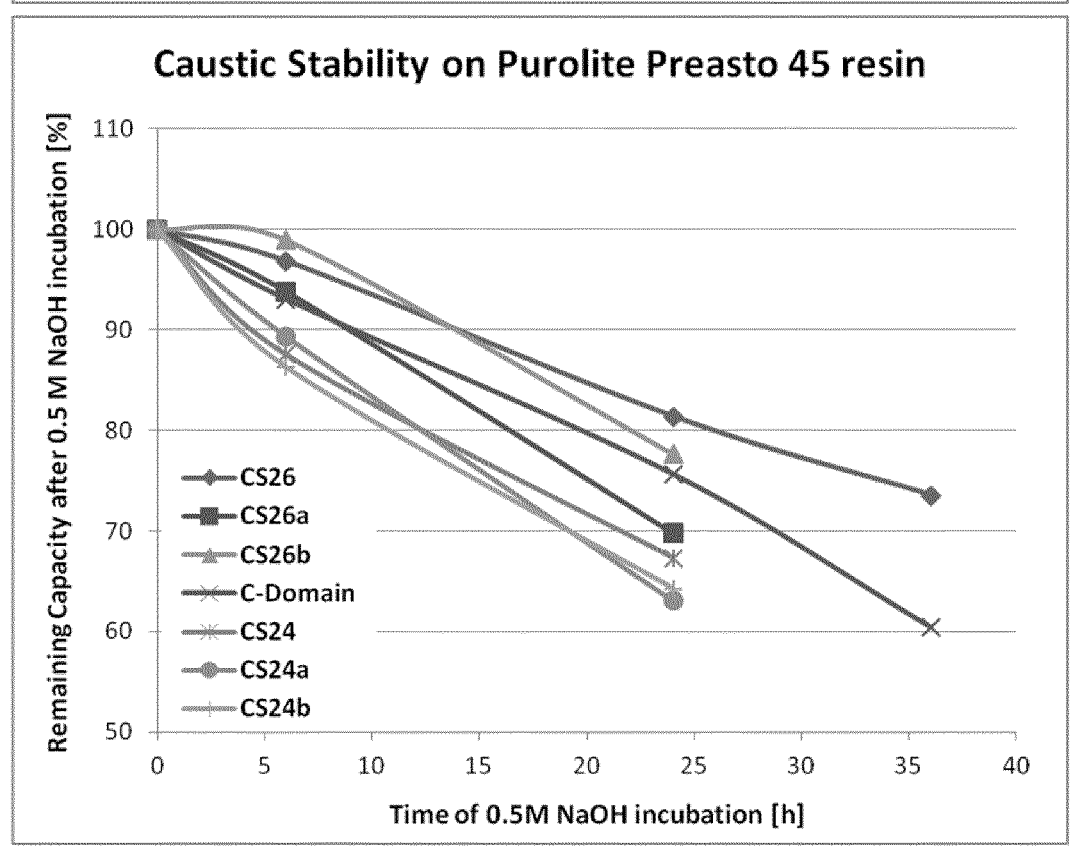

FIG. 2 shows that the activity of Fc binding proteins SEQ ID NOs: 1-6 is very high even after incubation for 6 h at 0.5 M NaOH (at least 87.6% remaining activity for all Fc binding proteins SEQ ID NOs: 1-6 after 6 h incubation at 0.5 M NaOH). All Fc binding proteins of the invention show significantly high stability at high pH. FIG. 3 further shows results from Praesto™ Pure45 matrix and Praesto™ Pure85 matrix.

Example 9. Elution of hIgG from Fc Binding Proteins Coupled to Agarose-Based Chromatography Beads Praesto™ Pure45 and/or Pure85

Purified Fc binding proteins were coupled to agarose-based chromatography beads (Praesto™ Pure45 or Pure 5) according to the manufacturer's instructions. Polyclonal human IgG Gammanorm® was used as IgG sample (conc. 2.2 mg/ml), loading up to DBC10%. Polyclonal hIgG sample was applied in saturated amounts to the matrix comprising immobilized Fc binding protein. In a two-step process, the matrix was first washed with 100 mM Citrate buffer, pH 3.5 and then with 100 mM Citrate buffer, pH 2.0 to elute hIgG that was bound to the immobilized Fc binding protein.

Figure 4:
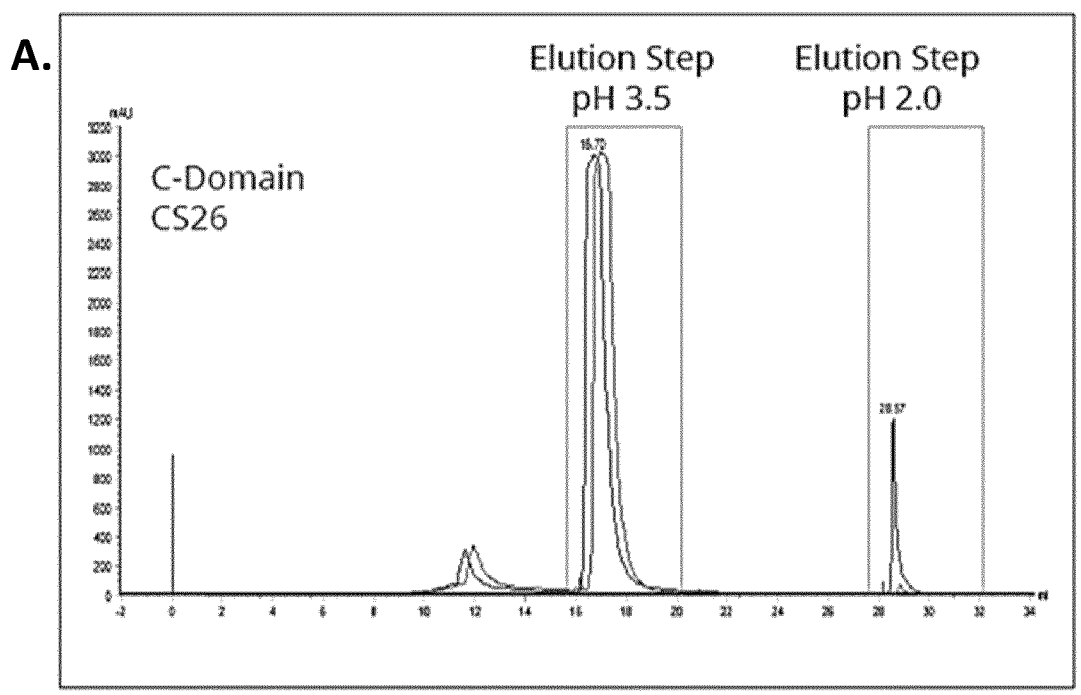
FIG. 4. Analysis of elution of polyclonal hIgG from Fc binding domains cs24 (SEQ ID NO: 1), cs24a (SEQ ID NO: 3), cs24b (SEQ ID NO: 5), cs26 (SEQ ID NO: 2), cs26a (SEQ ID NO: 4), and cs26b (SEQ ID NO: 6) at pH 3.5 and 2.0. Panel A shows a representative elution test. Step yield at 3.5 pH elution for all Fc domains was greater than 98% (panel B), far exceeding the elution of Protein A domain C.

As shown in FIG. 4, greater than 98% of the bound polyclonal human IgG was eluted at pH 3.5, which was considerably higher than elution from wild-type Protein A domain C.

The invention claimed is:

1. An Fc binding protein comprising one or more domains, wherein at least one domain comprises an amino acid sequence selected from any one of SEQ ID NOs: 1-6 and 21.

2. The Fc binding protein of claim 1, wherein the protein comprises 2, 3, 4, 5, or 6 domains linked to each other.

3. The Fc binding protein of claim 2, wherein all of the domains comprise sequences selected from any one of SEQ ID NOs: 1-6 and 21.

4. The Fc binding protein of claim 2, wherein the protein is a homo-multimer.

5. The Fc binding protein of claim 2, wherein the protein is a hetero-multimer.

6. The Fc binding protein of claim 2, wherein one or more domains are linked to each other directly or with one or more linkers.

7. The Fc binding protein of claim 6, wherein the linker is a peptide linker.

8. The Fc binding protein of claim 1, wherein the protein has less than a 15% reduction in binding capacity following an incubation in 0.5 M NaOH for at least 5 hours.

9. The Fc binding protein of claim 1, wherein the Fc binding protein is conjugated to a solid support.

10. The Fc binding protein of claim 9, wherein said Fc binding protein further comprises an attachment site for site-specific covalent coupling of the Fc binding protein to a solid support.

11. An affinity separation matrix comprising an Fc binding protein, the Fc binding protein comprising an amino acid sequence selected from any one of SEQ ID NOs: 1-6 and 21.

12. A method for affinity purification of a protein comprising an Fc sequence, the method comprising:
   (a) contacting an affinity separation matrix comprising at least one Fc binding protein with a solution containing a protein comprising an Fc sequence under conditions that permit binding of said at least one Fc binding protein to said protein comprising an Fc sequence, wherein the at least one Fc binding protein comprises an amino acid sequence selected from one of SEQ ID NOS: 1-6 and 21; and
   (b) eluting the bound protein comprising an Fc sequence from said affinity separation matrix.

13. The method of claim 12, further comprising washing the affinity separation matrix between steps (a) and (b).

14. The method of claim 12, wherein there is at least 95% elution of the protein comprising an Fc sequence at a pH of 3.5 or higher.

* * * * *